United States Patent
Meneses et al.

(10) Patent No.: US 7,337,616 B2
(45) Date of Patent: Mar. 4, 2008

(54) SYSTEM FOR SAMPLING CRYOGENIC LIQUIDS, AND AIR SEPARATION UNIT PROVIDED WITH AT LEAST ONE SUCH SYSTEM

(75) Inventors: David Meneses, Paris (FR); Jean-Yves Thonnelier, Voisins le Bretonneux (FR); Jean-Yves Lehman, Maisons Alfort (FR)

(73) Assignee: L'Air Liquide, Societe Anonyme A Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 750 days.

(21) Appl. No.: 10/424,059

(22) Filed: Apr. 25, 2003

(65) Prior Publication Data

US 2003/0228707 A1   Dec. 11, 2003

(51) Int. Cl.
*F17C 7/04* (2006.01)
*F17C 9/02* (2006.01)
*F17C 13/02* (2006.01)
*B32B 5/02* (2006.01)
*B32B 27/04* (2006.01)

(52) U.S. Cl. .................. 62/48.1; 62/49.1; 62/50.2; 62/600; 62/45.1; 62/617; 62/389; 422/50; 422/68.1; 422/83; 436/43; 436/127; 436/106; 436/116; 436/139; 436/145; 436/181

(58) Field of Classification Search ............... 62/48.1, 62/50.2, 600, 45.1, 617, 389; 422/50, 68.1, 422/83
See application file for complete search history.

(56) References Cited

U.S. PATENT DOCUMENTS 3,133,444 A    5/1964  Karwat
3,357,256 A *  12/1967 Burch ................ 73/863.11
3,673,871 A *  7/1972  Randle et al. ......... 73/863.12
3,696,627 A *  10/1972 Longsworth ............ 62/48.1
4,631,967 A    12/1986 Welker
4,991,449 A *  2/1991  Dieguez .............. 73/863.11
5,161,381 A    11/1992 Victor et al.
5,195,325 A    3/1993  Short et al.
5,255,523 A *  10/1993 Burgers et al. ........... 62/601
5,501,080 A *  3/1996  McManus et al. ........ 62/55.5
5,629,208 A    5/1997  Darredeau et al.
6,399,393 B1 * 6/2002  Doyle et al. ............ 436/174

FOREIGN PATENT DOCUMENTS

EP    0 345 164 A    12/1989
EP    0 726 434 A    8/1996
FR    1 329 313 A    6/1963
FR    2 637 982 A    4/1990
FR    2 786 858 A    6/2000

OTHER PUBLICATIONS

French Search Report to FR 02 05216.

* cited by examiner

*Primary Examiner*—Brian Sines
(74) *Attorney, Agent, or Firm*—Elwood Haynes

(57) ABSTRACT

A system for sampling cryogenic liquids, and an air separation unit provided with at least one such system. The cryogenic liquid is introduced into a vaporizer, through heat exchange with the compressed air. The liquid passes through the vaporizer generally downwards. The walls of the vaporizer that are intended to come into contact with the cryogenic liquid are maintained at a temperature above the sublimation temperature or the boiling point of the least volatile impurity contained in this liquid. Downstream of the vaporizer, a gaseous phase coming from the vaporization of the cryogenic liquid is withdrawn and at least some of the gaseous phase is sent to an analyzer.

13 Claims, 6 Drawing Sheets

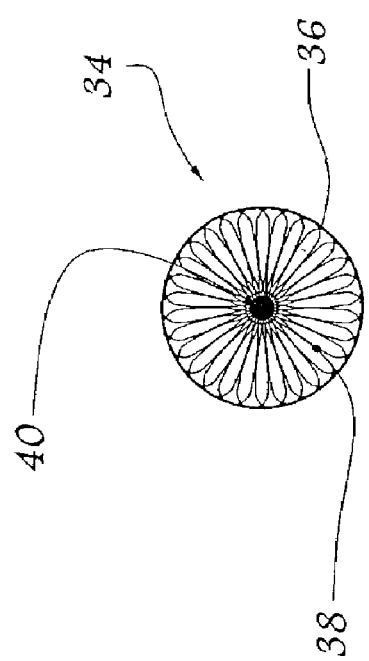
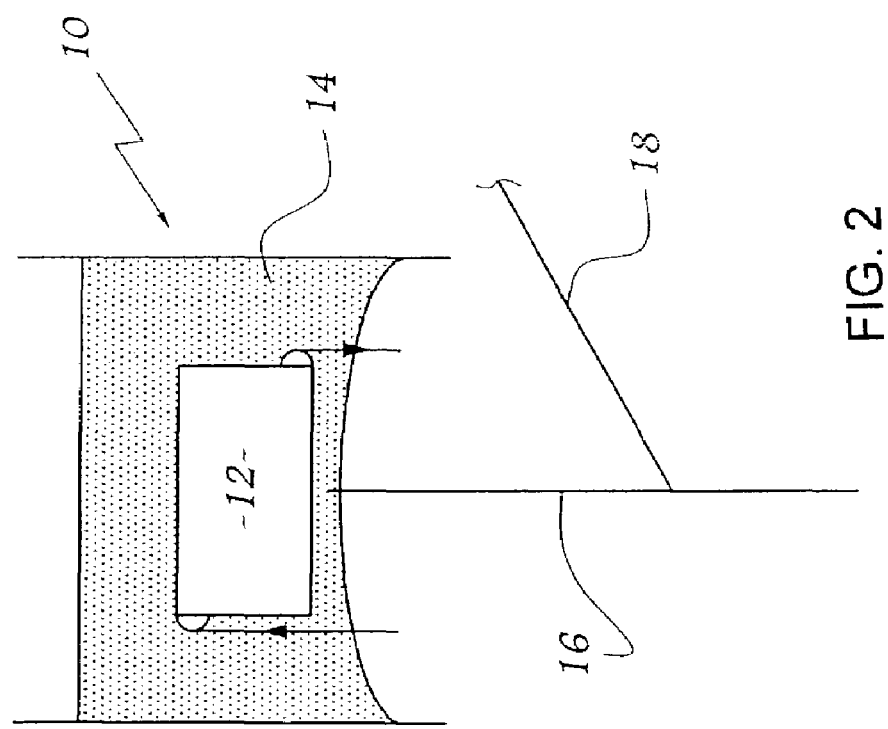

SYSTEM FOR SAMPLING CRYOGENIC LIQUIDS, AND AIR SEPARATION UNIT PROVIDED WITH AT LEAST ONE SUCH SYSTEM

This application claims the benefit of priority under 35 U.S.C. §119 (a) and (b) to French Application No. 0205216, filed Apr. 25, 2002, the entire contents of which are incorporated herein by reference.

BACKGROUND

The present invention relates to a method and a system for sampling cryogenic liquids and to an air separation unit provided with at least one such system.

Such cryogenic liquids, which are usually oxygen, nitrogen or argon, are at a temperature below about −170° C. They are in particular produced by the use of a distillation column forming part of an air separation unit.

It is known to take samples of these cryogenic liquids for the purpose of subsequently analysing them. This then makes it possible to check, in particular, the content of low-volatility impurities in these liquids, such as nitrous oxide $N_2O$, carbon dioxide $CO_2$ or hydrocarbons $C_nH_m$.

This is because, at cryogenic temperatures, some of these impurities are liable to be deposited in the components of the air separation units, in particular in the reboiler/condenser of the distillation columns. It is therefore essential to monitor the impurity content, both in terms of product quality and plant safety.

When it is a question of analysing impurities of low volatility, there is the difficulty of obtaining a vaporized sample that is as representative as possible of the liquid to be analysed.

This is because the analytical methods commonly used, such as gas chromatography or infrared spectroscopy, involve warming the specimen taken up to a temperature close to room temperature. For this purpose, it is first necessary to vaporize the cryogenic liquid sampled, and then warm it.

Under these conditions, to obtain an analysis representative of a bath of cryogenic liquid, it is necessary, on the one hand, to take from it a liquid sample representative of the average composition of the entire bath, and then to vaporize it rapidly and completely. In the case of the air separation unit, two cryogenic liquid sampling modes are known in particular.

The first of these, also called "liquid lift", is based on the thermosyphon effect. To achieve this, a by-pass is made for the liquid to be analysed, in which by-pass the flow is provided by the vaporization of a fraction of this liquid.

This liquid lift is diverted to the wall of the cold box of the air separation unit, within an insulated container, for example insulated by rockwool, so as to limit any heat influx. A continuous sample of the cryogenic liquid flowing in this lift is then vaporized in a finned atmospheric heat exchanger, associated with a mixer, which is commonly called "flash vaporization".

An alternative mode of sampling, also called capillary sampling, consists in withdrawing the liquid under pressure through a capillary, namely a first tube of small inside diameter, for example about 0.5 mm. This tube is then taken, in a second tube, of larger cross section, to a hot spot where all of the liquid to be analysed instantly vaporizes.

These known sampling systems are widespread and guarantee results that are generally satisfactory. However, they do have a number of drawbacks.

Thus, they may introduce a problem as to the representativeness of the sample taken, in particular as regards capillary sampling, since the capillary, if it is connected to a liquid bath, does not allow forced flow of the said liquid to be analysed.

Moreover, these systems are subject to ageing, particularly in the case of the liquid lift.

This is because, in the latter case, there is progressive ingress of moisture into the insulation chamber, causing the formation and then the build-up of ice. The heat influx then becomes such that the liquid flow may be affected thereby.

SUMMARY

The invention includes systems to achieve the desired results, as described, but is not limited to the various embodiments disclosed.

In one embodiment, a sampling system for sampling at least one cryogenic liquid, especially oxygen or nitrogen, containing impurities such as nitrous oxide, carbon dioxide or hydrocarbons is provided. This system includes a sampling line within which the cryogenic liquid is intended to flow. This sampling line may be connected to a flow line for at least one cryogenic liquid. This sampling line may be placed so that the flow of the liquid takes place generally upwards, with reference to the flow direction of the cryogenic fluid.

This system includes a vaporizer, which is connected to the sampling line so that at least one liquid passes through the vaporizer, generally downwards. This system includes a means for maintaining the walls of the vaporizer that are intended to come into contact with the cryogenic liquid at a temperature above the sublimation temperature or boiling point of the volatile impurity contained in the liquid. This system includes a means for withdrawing, downstream of the vaporizer, a gaseous phase coming from the vaporization of the cryogenic liquid. These withdrawal means may communicate with an analyzer. This system includes a means for controlling the flow rate of this gaseous phase.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein:

FIG. 2 is a schematic view, on a larger scale, illustrating the sampling of a cryogenic liquid according to an alternate embodiment of the present invention;

FIG. 4 is a cross-sectional view illustrating an alternative embodiment of a vaporizer forming part of the system of FIG. 1;

DESCRIPTION OF PREFERRED EMBODIMENTS

Figure 1:
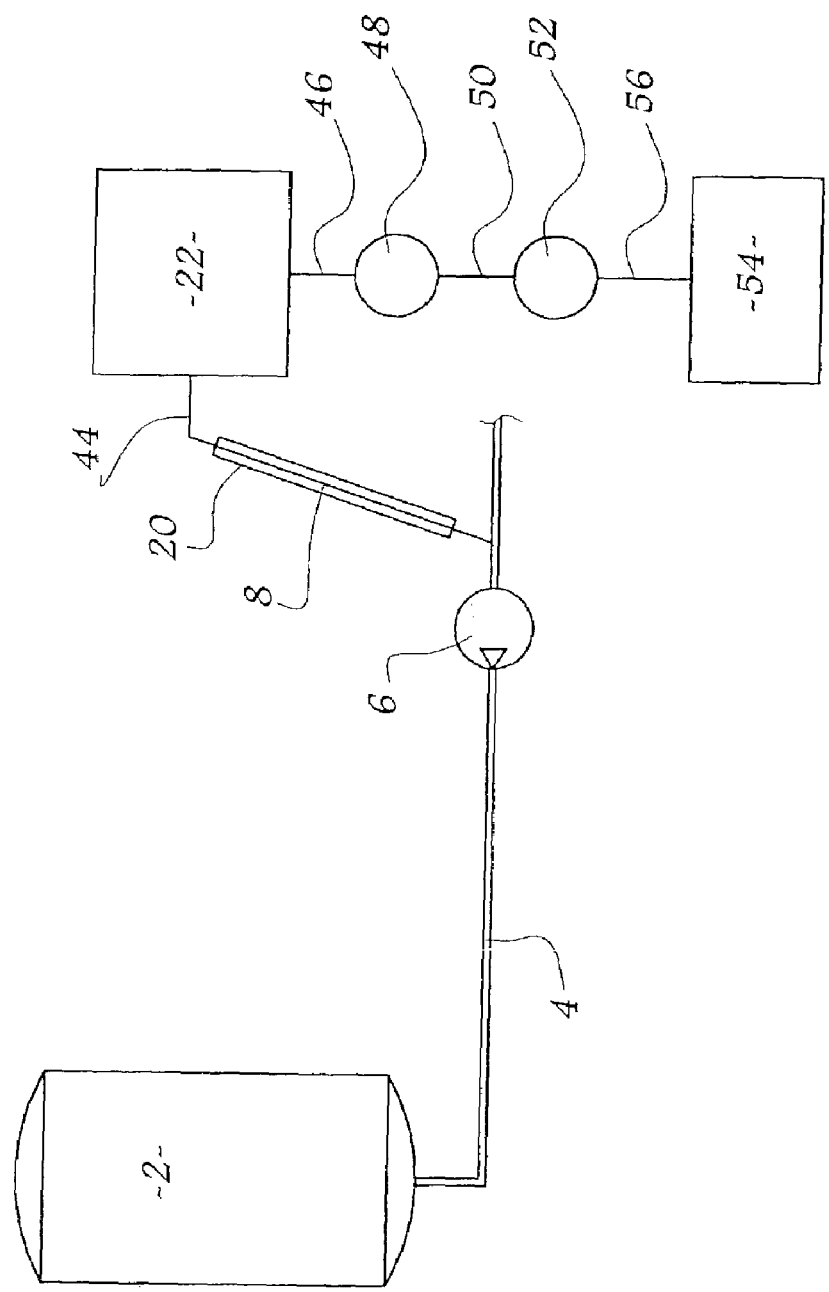
FIG. 1 is a schematic view illustrating an air separation unit provided with a cryogenic liquid sampling system according to one embodiment of the present invention.

The invention includes systems to achieve the desired results, as described, but is not limited to the various embodiments disclosed.

In one embodiment, a sampling system for sampling at least one cryogenic liquid, especially oxygen or nitrogen, containing impurities such as nitrous oxide, carbon dioxide or hydrocarbons is provided. This system includes a sampling line within which the cryogenic liquid is intended to flow. This sampling line may be connected to a flow line for at least one cryogenic liquid. This sampling line may be placed so that the flow of the liquid takes place generally upwards, with reference to the flow direction of the cryogenic fluid.

This system includes a vaporizer, which is connected to the sampling line so that at least one liquid passes through the vaporizer, generally downwards. This system includes a means for maintaining the walls of the vaporizer that are intended to come into contact with the cryogenic liquid at a temperature above the sublimation temperature or boiling point of the volatile impurity contained in the liquid. This system includes a means for withdrawing, downstream of the vaporizer, a gaseous phase coming from the vaporization of the cryogenic liquid. These withdrawal means may communicate with an analyzer. This system includes a means for controlling the flow rate of this gaseous phase.

Under these conditions, the aim of the invention is to implement a method for reliably sampling a cryogenic liquid, while using a system requiring only little maintenance. FR-A-1329313 discloses a method according to the preamble of claim 1 and provides for the cryogenic liquid to be vaporized by heat exchange with a hot fluid.

For this purpose, it is an object of the invention to provide a method of sampling at least one cryogenic liquid, especially oxygen or nitrogen, containing impurities such as nitrous oxide, carbon dioxide or hydrocarbons, comprising the following steps:
- the or each cryogenic liquid is let into a vaporizer, which communicates with the sampling line via a connection region, so that the or each cryogenic liquid passes through the vaporizer generally downwards;
- those walls of the said vaporizer that are intended to come into contact with the or each cryogenic liquid are maintained at a temperature above the sublimation temperature or the boiling point of the least volatile impurity contained in this liquid; and
- downstream of the vaporizer, a gaseous phase coming from the vaporization of the or each cryogenic liquid is withdrawn, at least part of this gaseous phase being intended to be sent to an analyser;
- characterized in that the or each liquid vaporizes in the vaporizer by heat exchange with the atmosphere.

According to other features of the invention:
- the or each cryogenic liquid is taken off downstream of a pump, before being made to flow through the sampling line;
- the or each cryogenic liquid is taken off into a purge line, extending from a bath of the or each liquid, before being made to flow through the sampling line;
- those walls of the connection region that are intended to come into contact with the or each cryogenic liquid are also maintained at a temperature above the sublimation temperature or the boiling point of the least volatile impurity contained in the liquid;
- the walls of the vaporizer and, if appropriate, the walls of the connection region are maintained at a temperature above −70° C.;
- downstream of the vaporizer, the gaseous phase is made to dwell in a mixing chamber;
- the flow rate of the gaseous phase is controlled, an optimum cryogenic liquid flow rate range regarding the sampling line and/or the vaporizer being determined, this optimum range is converted into a preferred gas flow rate range and the instantaneous gas flow, coming from the vaporizer, is maintained within this preferred gas flow rate range;
- the gaseous phase is made to dwell in this mixing chamber for at least 10 seconds;
- the liquid completely vaporizes in the vaporizer;
- the or each cryogenic liquid is made to flow within a sampling line, preferably so that the or each liquid runs through the line generally upwards;
- this sampling line is thermally insulated;
- the flow rate of the said gaseous phase is controlled; and
- the rate of vaporization in the sampling line is less than 50%.

It is another object of the invention to provide a system for sampling at least one cryogenic liquid, especially oxygen or nitrogen, containing impurities such as nitrous oxide, carbon dioxide or hydrocarbons, comprising:
- a sampling line within which the or each cryogenic liquid is intended to flow, it being possible for this sampling line to be connected to a flow line for the or each cryogenic fluid and preferably to be placed so that the flow of the liquid takes place generally upwards, with reference to the flow direction of the cryogenic liquid;
- optionally, means for thermally insulating this sampling line;
- a vaporizer, communicating with the sampling line so that the or each liquid passes through the vaporizer generally downwards;
- means for maintaining those walls of the said vaporizer that are intended to come into contact with the or each cryogenic liquid at a temperature above the sublimation temperature or boiling point of the least volatile impurity contained in this liquid;
- means for withdrawing, downstream of the vaporizer, a gaseous phase coming from the vaporization of the or each cryogenic liquid, it being possible for these withdrawal means to communicate with an analyser; and
- means for controlling the flow rate of this gaseous phase;
- characterized in that the vaporizer is provided with means for increasing the heat exchange between its walls and the atmosphere.

According to other features of the invention:
- the means for thermally insulating the sampling line include at least one cryogenic insulation layer;
- the means for thermally insulating the sampling line include a guard line placed around this sampling line, and flowing in this guard line is another cryogenic fluid allowing the heat influx to be absorbed;
- the sampling line is a vacuum-insulated line;
- the walls of the vaporizer define an internal volume for the flow of the or each cryogenic liquid and, within this internal volume, means are provided for increasing the heat exchange between the cryogenic liquid and these walls;
- the vaporizer is a plate heat exchanger provided with internal fins and, optionally, external fins;
- the vaporizer is a tube heat exchanger provided with internal fins and, optionally, external fins;

the system furthermore includes, placed downstream of the vaporizer, means for mixing the gaseous phase, especially a mixing chamber;

the means for controlling the flow rate of the gaseous phase comprise a mass flow regulator;

the vaporizer is in the open air;

the vaporizer includes obstacles to the vertical flow, preferably not allowing the accumulation of liquid;

the obstacles form an integral part of or are in thermal contact with the walls of the vaporizer.

Finally, it is an object of the invention to provide an air separation unit, comprising at least one distillation column, from which at least one line for the flow of at least one cryogenic liquid extends, characterized in that at least one flow line communicates with a sampling system as defined above.

According to another feature of the invention, the flow line is located downstream of a pump, or the flow line is a purge line.

FIG. 1 illustrates, in part, an air separation unit of known type.

This unit includes in particular a distillation column 2 from which extends an output line 4 in which a cryogenic liquid, for example oxygen, flows. As a variant, this line could convey another type of cryogenic liquid, in particular nitrogen.

The line 4 is provided with a pump 6, ensuring production or recirculation. Provided downstream of this pump 6 is a line 8 for sampling the cryogenic liquid flowing in the line 4.

Such an arrangement of the sampling line 8, downstream of the pump 6, is advantageous since this downstream region is the most appropriate one for such sampling to be carried out, given that the flow rate of liquid flowing in it is high, the pressure of the liquid is high, and this liquid is subcooled.

This is because, given the pumping action, the cryogenic liquid is at a temperature below its actual equilibrium temperature. As a result, this subcooling reduces the risk of undesirable accidental vaporization of the cryogenic liquid and thus improves the quality of the sampling.

FIG. 2 illustrates one embodiment relating to the arrangement of this sampling line.

Shown schematically in this FIG. 2 is a reboiler/condenser 10 forming part of the distillation column 2. This reboiler/condenser, known per se, is provided with a heat exchanger 12 which is immersed in a bath 14 of liquid oxygen.

As is known per se, a purge line 16, for reducing the concentration of low-volatility impurities in the bath 14, extends downwards from the bottom of this bath. It is therefore possible to tap off this purge line 16 a sampling line 18, similar to the line 8 illustrated in FIG. 1.

The embodiment in FIG. 2 is advantageous in so far as the liquid flowing in the purge line 16 is representative of the bath 14 to be analysed. Given that this purge line 16 is also placed at the bottom of the bath, the liquid flowing out of it is also subcooled owing to the influence of the hydrostatic pressure.

Referring once again to FIG. 1, the sampling line 8 runs upwards, with reference to the direction of flow of the liquid, indicated by the arrow f.

Such an arrangement of the sampling line is advantageous given that it avoids the existence of low points when taking the liquid to the vaporizer, which will be described below. In this way it is possible to avoid any accumulations of impurity deposits in solid or liquid form, since the liquid/gas front is minimized.

The sampling line 8 is also provided with thermal insulation means, indicated by the reference 20.

These insulation means may consist of a simple cryogenic insulation, for example formed from one or more layers of insulating foam combined with an insulating jacket.

As an alternative, the use of a guard liquid may be envisaged. In this case, the sampling line 8 is surrounded by a peripheral sheath (not shown in FIG. 1) in which another cryogenic liquid, intended to absorb the heat influx, flows.

As a further alternative, the sampling line 8 may be produced, in a manner known per se, in the form of a vacuum-insulated line.

It should be noted that the various embodiments described above with reference to the sampling line 8 of FIG. 1 may be applied in a similar manner to the sampling line 18, illustrated in FIG. 2.

Once again referring to FIG. 1, the cryogenic liquid, taken off via the line 8, is sent to a vaporizer 22.

Figure 3:
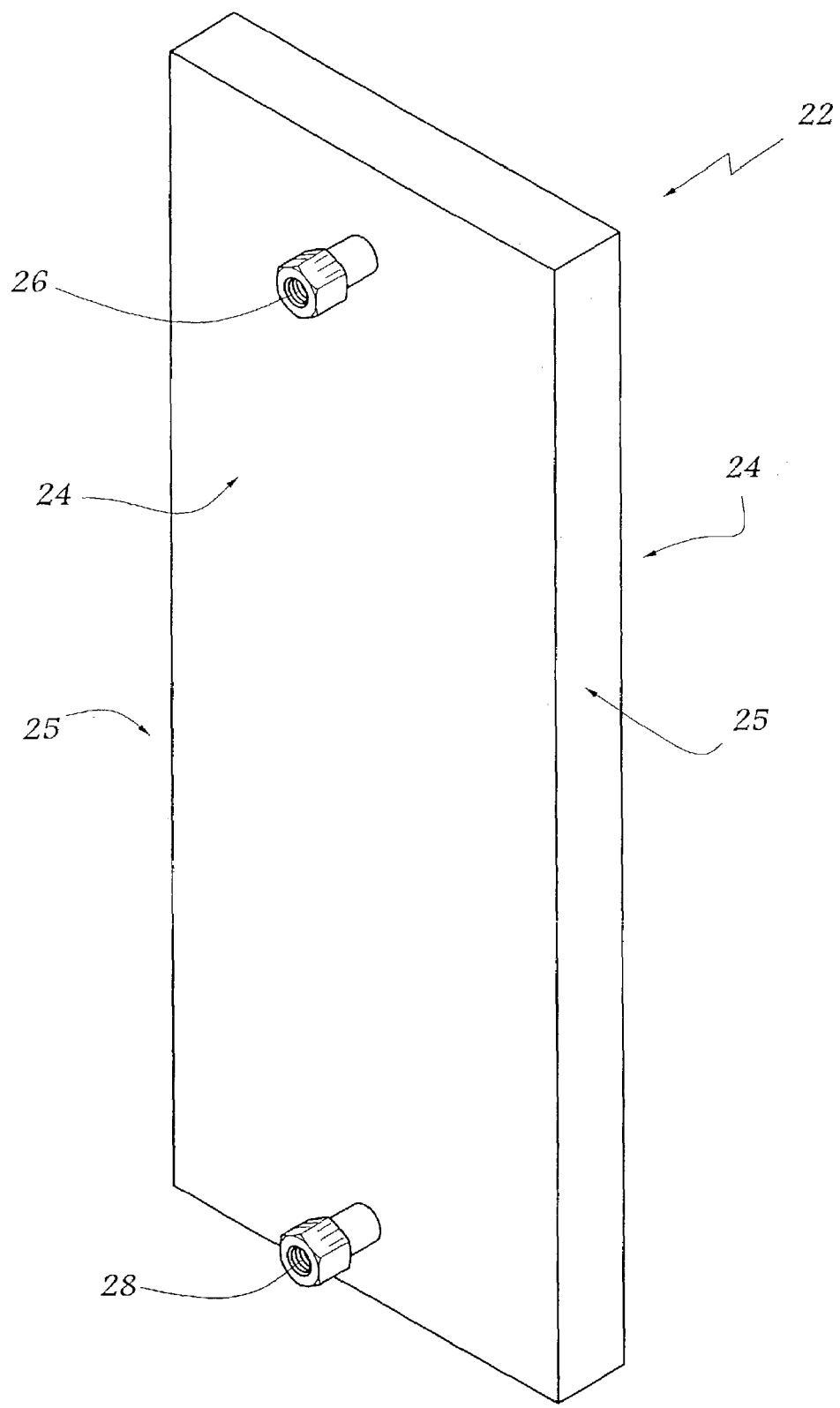
FIG. 3 is a perspective view illustrating a first embodiment of a vaporizer forming part of the system of FIG. 1.

The latter, which is illustrated more precisely in FIG. 3, is a plate heat exchanger made of brazed aluminium, the technology of which is widely used in the cryogenic industry.

This heat exchanger 22 comprises two main plates 24 which, together with side plates 25, define an internal volume V for flow of cryogenic liquid. This vaporizer 22 is also provided with at least one liquid inlet 26, at the top, and with at least one gas outlet 28, at the bottom, so as to make the liquid in the volume V flow vertically downwards.

Internal finning placed in the internal volume V act as obstacles to the direct passage of the liquid from the top down, and allow the heat transmitted by the main plates 24 to be effectively transferred. Thus, the liquid vaporizes almost completely during its descent.

Figure 5:
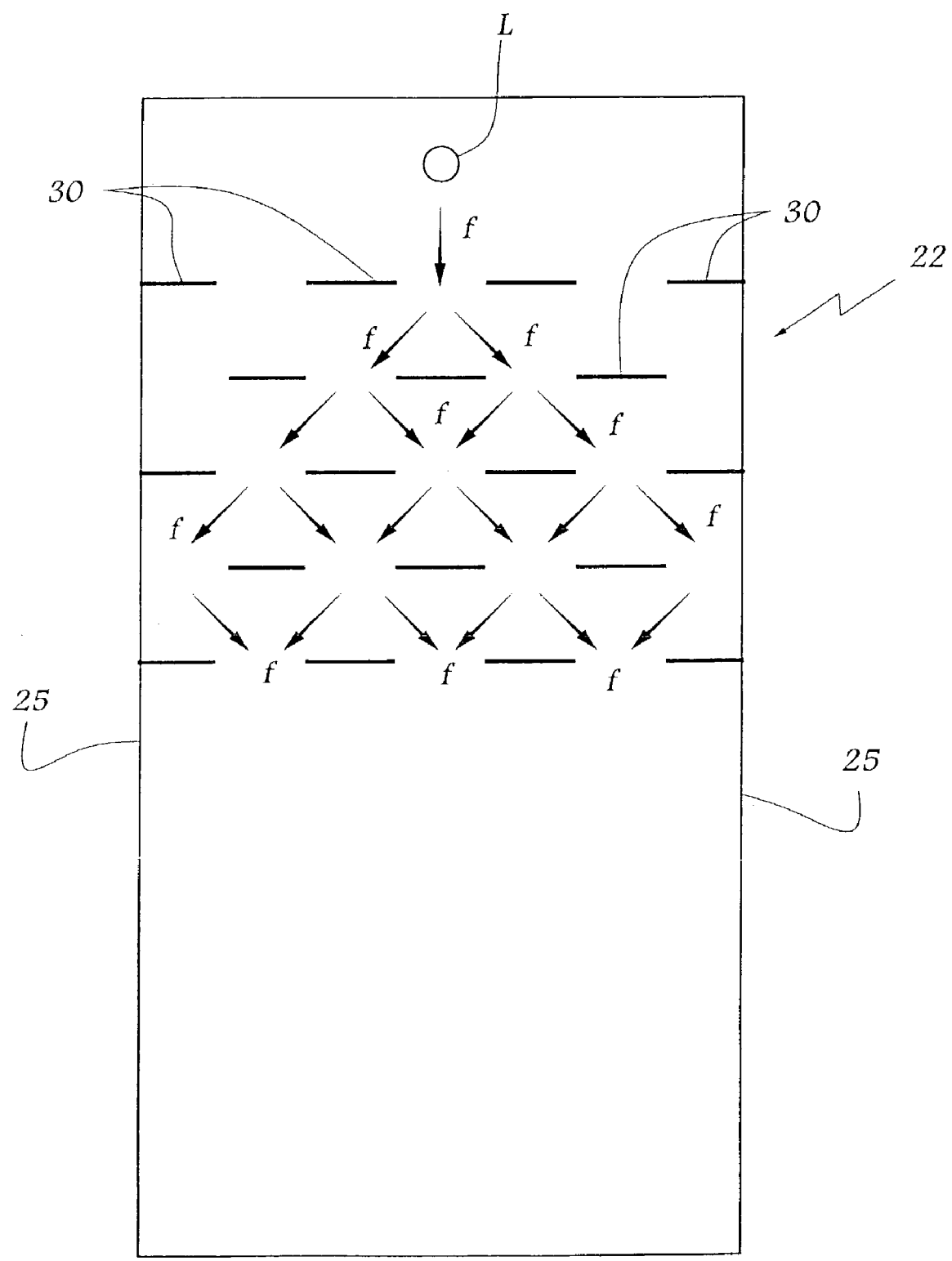
FIG. 5 is a longitudinal sectional view illustrating the vaporizer of FIG. 3.

As shown in FIG. 5, this internal finning 30 is of the "serrated" type, in the "hardway" position, and define a structure of staggered horizontal fins. This structure divides an incoming drop of liquid L into a multiplicity of droplets, indicated by the arrows f, which vaporize on descending, with no possibility of liquid accumulating in pockets.

Returning to FIG. 3, the plates 24 of the vaporizer 22 may advantageously be provided with external fins (not shown) of appropriate shape, so as to increase the heat exchange with the ambient air. However, the risk of these external fins becoming blocked by ice should not be ignored.

In accordance with the method of the invention, those walls of the exchanger 22 that are intended to come into contact with the liquid to be vaporized are maintained at a temperature above the sublimation temperature or the boiling point of the least volatile impurity contained in this cryogenic liquid.

This is because the drops of liquid containing the impurities to be analysed consist of molecules that are more volatile than these various impurities. There is therefore a risk of their vaporization, within the heat exchanger 22, causing the formation of solid deposits, in the form of crystals, or liquid deposits which have a tendency to build up on the internal walls of the heat exchanger.

Under these conditions, if these walls are maintained at a sufficiently high temperature then the solid deposits sublime, or else the liquid deposits vaporize. Consequently, the accumulation of such deposits is avoided, thereby guaranteeing good quality of the analysis carried out downstream of the heat exchanger 22.

Various solutions may be envisaged for maintaining the aforementioned walls within the abovementioned temperature range.

Thus, it is firstly possible for the actual arrangement or design of the heat exchanger to be such that, by simple exchange with the atmosphere, its walls are permanently within such a temperature range.

Alternatively, it is also conceivable to supply, from the outside, heat to the heat exchanger 22, for example in very cold and/or very wet regions. In this regard, it is possible to make a dry preheated gas undergo forced circulation around the heat exchanger 22, or else to heat the walls of this heat exchanger by an electrical device.

As a non-limiting example, when the impurities present in the cryogenic liquid are nitrous oxide $N_2O$, carbon dioxide $CO_2$ and hydrocarbons $C_nH_m$ for example, the temperature of those surfaces (walls and/or fins) of the heat exchanger that are in contact with the liquid should advantageously be brought to a value greater than about −70° C.

Alternatively, other types of heat exchanger, differing from that illustrated in FIG. 3, may be used.

Thus, it is possible to use a vaporization system called "flash vaporization", of a type known per se.

It is also conceivable to use a tube heat exchanger 34 (seen in FIG. 4).

This heat exchanger 34 comprises a main tube 36, defining an internal volume V' for flow of the cryogenic liquid.

This volume V' is partly occupied by internal fins 38, in the form of loops, which extend from the tube 36, around a central rod 40. Moreover, external fins (not shown) may also be advantageously provided.

Figure 6:
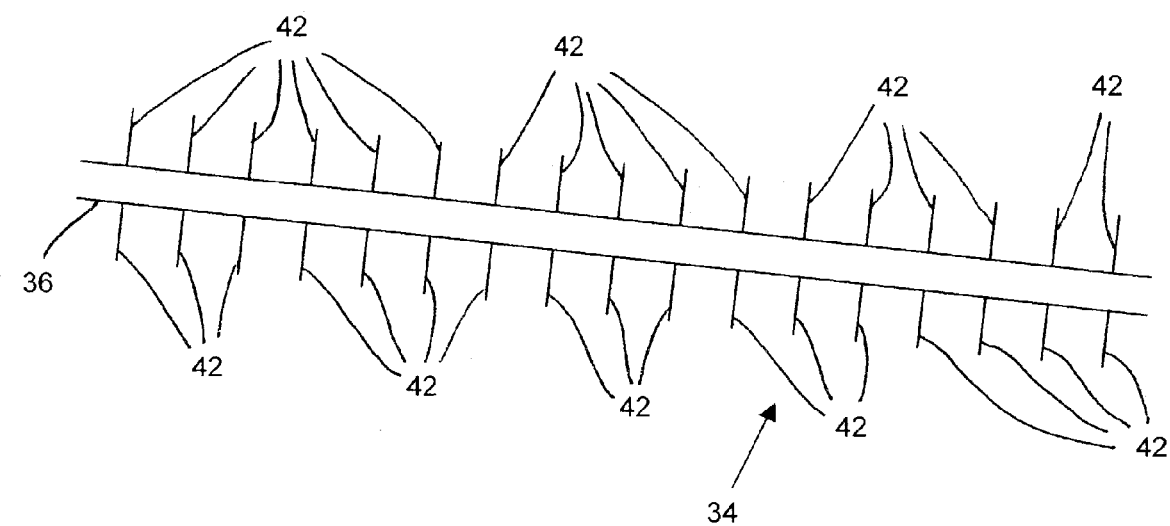
FIG. 6 is a variant of the vaporizer of FIGS. 3 and 5.
Figure 7:
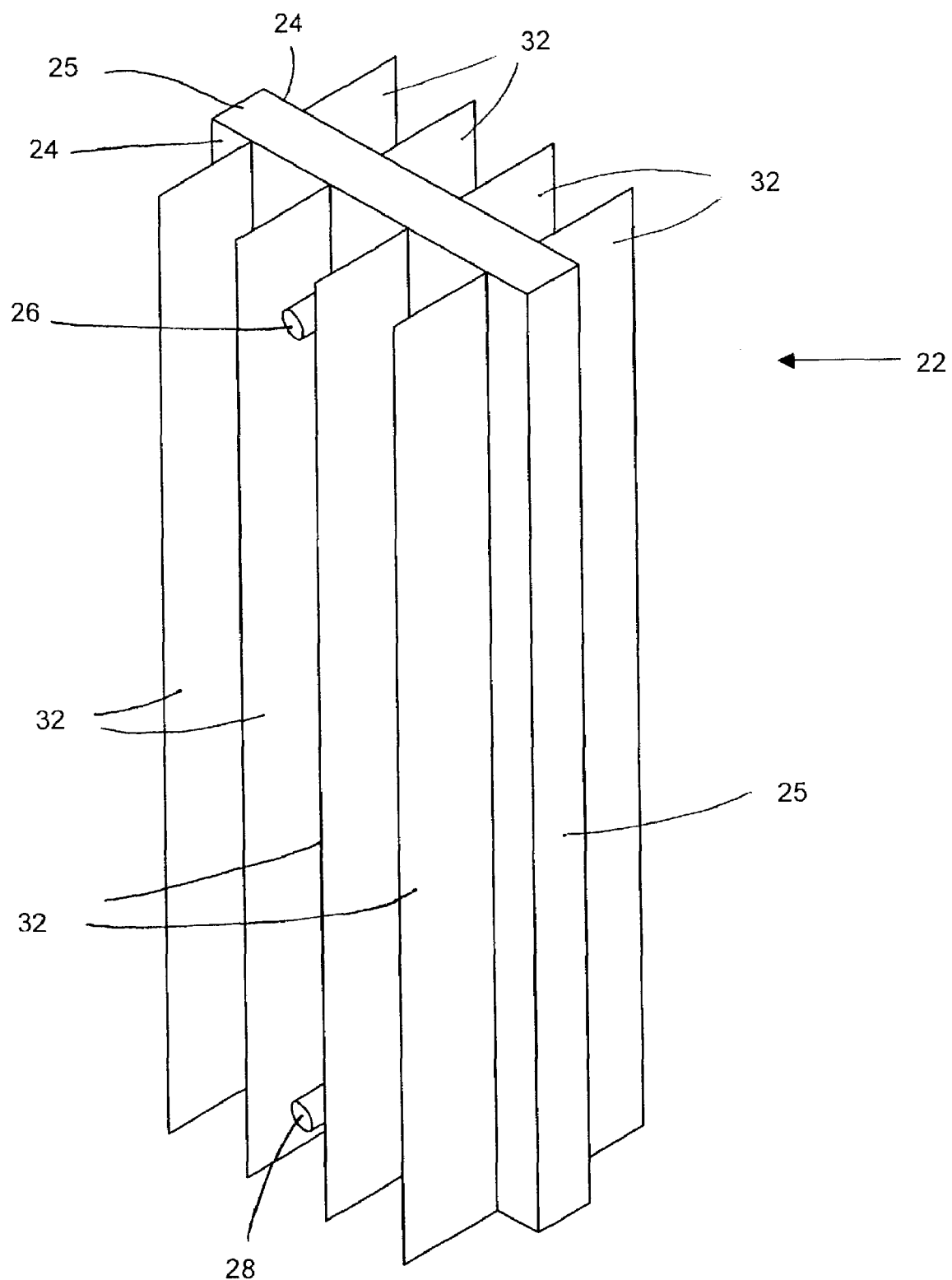
FIG. 7 is a variant of the vaporizer of FIGS. 3 and 5.

It should be noted that in FIGS. 6 and 7 not only is the plate exchanger 22 provided with external fins, but also the tube exchanger 34, these being 32 and 42 respectively. When designing these fins, it is recommended to be sure that their spacing is such that it prevents the formation of a solid layer of ice. Both of these vaporisers are designed to be in direct contact with ambient air.

Once again referring to FIG. 1, the cryogenic liquid is made to flow through the vaporizer 22 in a generally vertical and downward direction.

This arrangement makes it possible to prevent successive drops of cryogenic liquid coming into mutual contact. This therefore prevents any enrichment with low-volatility compounds, such as nitrous oxide $N_2O$ or carbon dioxide $CO_2$, in some of the drops.

In this way, the peaks in the contents of these impurities are avoided, thereby ensuring that the analysis is reliable.

As illustrated in FIG. 1, the connection region, labelled by the reference 44, brings the sampling line 18 into communication with the vaporizer 22.

This is a relatively awkward region as regards maintenance of the sampling system since solid impurities are more particularly liable to form or be deposited in this region 44.

To obviate such risks, it is advantageous to maintain the walls of this connection region 44 at a temperature above the sublimation temperature or the boiling point of the least volatile impurity contained in the cryogenic liquid.

Such an arrangement may be implemented in accordance with what was described above with regard to the walls of the vaporizer 22.

Thus, the arrangement of the connection region 44 may be designed in an appropriate manner so as to avoid the presence of regions where the fluid stagnates, or flows back on itself. In this regard, it is advantageous to use a flush liquid inlet.

Another possibility consists in making this connection region 44 at least partly of a material having a high thermal conductivity.

Again with reference to FIG. 1, the downstream end of the vaporizer 22 communicates via a line 46 with a mixing chamber 48.

It is advantageous to make the vaporized fraction coming from the heat exchanger 22 remain in this chamber, for example for a period of at least 10 seconds. This makes it possible to reduce the fluctuations in the analysis signal that are inherent in the discrete sublimation of solid deposits or the discrete vaporization of liquid deposits.

Alternatively, if such a chamber 48 is not used, it is necessary to smooth the signal obtained by the analyser.

Provided downstream of the chamber 48 is a line 50 that runs into a device 52 for regulating the flow rate of the gas flowing downstream of the heat exchanger 22.

Such a device advantageously consists of a mass flow regulator. Alternatively, it is also possible to use, for example, a rotameter.

According to the method of the invention, a liquid flow rate range is firstly determined for which the performance of the sampling line 18 and of the vaporizer 22 is optimum. This liquid flow rate range is then converted into a preferred gas flow rate range and the flow coming from the vaporizer 22 is regulated, by the device 52, so that it remains within this preferred range.

Such a control of the gas flow rate is relatively easy to implement. It also ensures that the vaporization of the cryogenic liquid proceeds effectively and satisfactorily and that the subsequent analysis is of high quality.

As a non-limiting example, it is advantageous to maintain the flow rate of the vaporized gas fraction, admitted downstream of the heat exchanger 22, within the range between 500 and 1,000 Sl/h.

Finally, downstream of the flow regulator 52, the gas stream is sent via a line 56 to at least one analyser 54. Such analysis carried out in a manner known per se.

It should be noted that the gas flow rate is set by the desired transit time of the sample, and not by the requirements of the analyser(s). In this regard, provision may be made for any excess flow to be vented, as a safety precaution.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A sampling system for sampling a cryogenic liquid of at least one of oxygen and nitrogen containing impurities of at least one of nitrous oxide, carbon dioxide and hydrocarbons, comprising:

a flow line adapted to flow the cryogenic liquid;

a sampling line connected at a first end to the flow line and adapted to flow at least portions of the cryogenic liquid from the flow line, wherein the sampling line is connected to the flow line such the at least portions of the cryogenic liquid flows in a first direction towards a second end of the sampling line, the first direction being generally upwards relative to a flow direction of the cryogenic fluid;

a vaporizer fluidly coupled to the second end of the sampling line, wherein the vaporizer comprises at least one wall and is configured to increase a heat exchange between the at least one wall and a surrounding atmosphere, and wherein the at least portions of the cryogenic liquid passes through the vaporizer in at least a second direction, generally opposite the first direction, and comes into contact with the at least one wall and vaporizes into a gaseous phase;

means for maintaining the at least one wall at a temperature above at least one of a sublimation temperature and a boiling point temperature of a least volatile impurity contained in the cryogenic liquid;

means for withdrawing the gaseous phase from a downstream end of the vaporizer and for introducing the gaseous phase to an analyzer; and means for controlling the flow rate of the gaseous phase.

2. The sampling system of claim 1, further comprising means for thermally insulating the sampling line.

3. The sampling system of claim 1, wherein the at least one wall defines an internal volume for flow of the at least portions of cryogenic liquid and wherein means are provided in the internal volume for increasing a heat exchange between the at least portions of cryogenic liquid and the at least one wall.

4. The sampling system of claim 2, wherein the at least one wall defines an internal volume for flow of the at least portions of cryogenic liquid and wherein means are provided in the internal volume for increasing a heat exchange between the at least portions of cryogenic liquid and the at least one wall.

5. The sampling system of claim 1, wherein the vaporizer is in open air.

6. The sampling system of claim 1, wherein the vaporizer further comprises obstacles to a flow of the at least portions of the cryogenic liquid.

7. The sampling system of claim 6, wherein the obstacles prevents accumulation of the at least portions of the cryogenic liquid.

8. The sampling system according to claim 6, wherein the obstacles are in thermal contact with the at least one wall.

9. An air separation unit, comprising at least one distillation column fluidly coupled to the sampling system according to claim 1.

10. An air separation unit, comprising at least one distillation column fluidly coupled to the sampling system according to claim 4.

11. The air separation unit according to claim 10, wherein the flow line is located downstream of a pump.

12. The air separation unit according to claim 10, wherein the flow line is a purge line.

13. A method of sampling a cryogenic liquid of at least one of oxygen and nitrogen containing impurities of at least one of nitrous oxide, carbon dioxide and hydrocarbons, comprising:

flowing the cryogenic fluid through a flow line;

flowing at least portions of the cryogenic liquid from the flow line through a sampling line connected at a first end to the flow line, wherein the sampling line is connected to the flow line such that the at least portions of the cryogenic liquid flows in a first direction from the first end towards a second end of the sampling line, the first direction being generally upwards relative to a flow direction of the cryogenic fluid;

flowing the at least portions of the cryogenic liquid into a vaporizer fluidly coupled to the second end of the sampling line, wherein the vaporizer comprises at least one wall and is configured to increase a heat exchange between the at least one wall and a surrounding atmosphere, and wherein the at least portions of the cryogenic liquid passes through the vaporizer in at least a second direction, generally opposite the first direction, and comes into contact with the at least one wall and vaporizes into a gaseous phase;

maintaining the at least one wall at a temperature above at least one of a sublimation temperature and a boiling point temperature of a least volatile impurity contained in the cryogenic liquid;

withdrawing the gaseous phase from a downstream end of the vaporizer;

controlling a flow rate of the gaseous phase; and introducing the withdrawn gaseous phase to an analyzer.

* * * * *